(12) United States Patent
Sofue et al.

(10) Patent No.: US 7,147,868 B2
(45) Date of Patent: Dec. 12, 2006

(54) ANTACID AND LAXATIVE TABLETS

(75) Inventors: Mitsuhiro Sofue, Kagawa (JP); Isamu Kawamura, Kagawa (JP); Shigeo Yamao, Kagawa (JP); Hideaki Baba, Kagawa (JP); Shiro Horie, Kagawa (JP); Yoko Abe, Kagawa (JP); Hisae Sofue, Kagawa (JP)

(73) Assignee: Kyowa Chemical Industry Co., Ltd., Kagawa (JP)

( * ) Notice: Subject to any disclaimer, the term of this patent is extended or adjusted under 35 U.S.C. 154(b) by 690 days.

(21) Appl. No.: 10/380,407

(22) PCT Filed: Jul. 8, 2002

(86) PCT No.: PCT/JP02/06909

§ 371 (c)(1),
(2), (4) Date: Jun. 10, 2003

(87) PCT Pub. No.: WO03/018034

PCT Pub. Date: Mar. 6, 2003

(65) Prior Publication Data

US 2004/0022872 A1    Feb. 5, 2004

(30) Foreign Application Priority Data

Aug. 27, 2001  (JP)  ............................. 2001-256421

(51) Int. Cl.
*A61K 9/14*   (2006.01)
*A61K 9/20*   (2006.01)
*A61K 9/46*   (2006.01)

(52) U.S. Cl. ........................ 424/466; 424/464; 424/489
(58) Field of Classification Search ..................... None
See application file for complete search history.

(56) References Cited

U.S. PATENT DOCUMENTS

| 4,921,707 A | | 5/1990 | Racz et al. | |
|---|---|---|---|---|
| 5,039,509 A | * | 8/1991 | Miyata et al. | 423/636 |
| 5,320,852 A | * | 6/1994 | Moest | 424/464 |

FOREIGN PATENT DOCUMENTS

EP    0 524 696    1/1993

* cited by examiner

*Primary Examiner*—S. Tran
(74) *Attorney, Agent, or Firm*—Wenderoth, Lind & Ponack, L.L.P.

(57) ABSTRACT

An antacid and laxative tablet comprising magnesium oxide particles as an effective component, wherein
(i) the magnesium oxide particles contained in the tablet have an average secondary particle diameter measured by a laser diffraction scattering method of 0.5 to 10 μm,
(ii) the content of magnesium oxide particles in the tablet is 88 wt % or more,
(iii) the tablet does not become blackish and has substantially no tableting spot, and
(iv) the disintegration time is 10 sec or less.

The antacid and laxative tablet of the present invention has a high content of magnesium oxide particles, a short disintegration time, does not become blackish, has no tablet trouble and no tableting spot and is suitably administered orally.

9 Claims, No Drawings

ANTACID AND LAXATIVE TABLETS

DETAILED DESCRIPTION OF THE INVENTION

1. Field of the Invention

The present invention relates to an antacid and laxative tablet used for hyperacidity, acid secretion sthenia or constipation and, specifically, to a magnesium oxide particle-containing tablet which does not become blackish, is substantially free from a tablet trouble and a tabuleting spot, has a high content of magnesium oxide particles and is easily taken because it disintegrates quickly in the mouth when it is administered together with water. More specifically, it relates to an antacid and laxative magnesium oxide particle-containing tablet which has a magnesium oxide particle content of 88 wt % or more and a disintegration time of 10 sec or less.

2. Description of the Prior Art

Since conventional magnesium oxide particle-containing tablets are prepared by blending an excipien, binder, disintegrator and lubricant with granular magnesium oxide particles in accordance with a direct tableting method. Since the magnesium oxide particles are hard, they wear down a tablet machine and cause the production of a blackish tablet and the formation of a tabulating spot.

When the tableting pressure is reduced to make tablets in order to prevent these, compactibity lowers, thereby making impossible tableting.

Tabulet troubles such as sticking caused by the adhesion of magnesium oxide particles at the time of tableting and capping caused by the deterioration of a die and punch may occur. In this case, the durability of the die and punch is reduced by the abrasion of the magnesium oxide particles and production cost is boosted.

In order to prevent these troubles in making tablets as much as possible, there is a method of preparing tablets using special additives. A tablet of hard magnesium oxide particles has a long disintegration time and shows antacid and laxative effects slowly. When the tablet has a high content of magnesium oxide particles, it may fail to disintegrate because it does not disintegrate quickly. To prevent this, the tablet contains a large amount of a disintegrator, which reduces the content of the magnesium oxide particles in the tablet.

To prepare a magnesium oxide particle-containing tablet in the prior art, additives such as a binder and a disintegrator are mixed with magnesium oxide particles and the resulting mixture is tableted (for example, JP-A 9-40561 and JP-A 2001-48792).

According to the above publications, carboxymethyl cellulose sodium, low-substituted hydroxypropyl cellulose or crystalline cellulose is used as a binder and contained in an amount of 1 to 10 wt %, particularly 1 to 5 wt % based on the tablet.

Carboxymethyl cellulose calcium, carmerose or low-substituted hydroxylpropyl cellulose is used as a disintegrator and contained in an amount of 5 to 20 wt %, particularly 5 to 10 wt % based on the tablet.

SUMMARY OF THE INVENTION

It is an object of the present invention to provide a tablet which has a high content of magnesium oxide particles, that is, low contents of additives, has a short disintegration time, is easily prepared because magnesium oxide particles do not wear down a tablet machine and are not adhered to a die and punch substantially at the time of preparation, and is easily taken when it is administered.

The inventors of the present invention have conducted studies on the physical properties of magnesium oxide particles and additives to attain the above object of the present invention. As a result, we have found that the average secondary particle diameter of magnesium oxide particles and the types and amounts of additives (binder, disintegrator) have an influence upon the tableting properties and disintegration of a magnesium oxide tablet.

In other words, studies conducted by the inventors of the present invention have revealed that a tablet having a high content of magnesium oxide particles and a very short disintegration time is obtained by selecting a combination of magnesium oxide particles having a specific form and specific additives, that the magnesium oxide particles do not wear down a tablet machine at the time of tabuleting and are hardly adhered to a die and punch and that a tablet which does not become blackish and has substantially no tableting spot is obtained. The present invention has been accomplished based on these findings.

Means to Solve the Problems

According to the present invention, there is provided a tablet comprising magnesium oxide particles as an effective component, which is an antacid and laxative tablet wherein (i) the magnesium oxide particles contained in the tablet have an average secondary particle diameter measured by a laser diffraction scattering method of 0.5 to 10 µm, (ii) the content of magnesium oxide particles in the tablet is 88 to 97 wt %, (iii) the tablet does not become blackish and has substantially no tableting spot, and (iv) the disintegration time is 10 sec or less.

The antacid and laxative tablet of the present invention and the production process therefor of the present invention will be described in detail hereinunder.

The magnesium oxide particles in the present invention have an average secondary particle diameter measured by the laser diffraction scattering method of 0.5 to 10 µm, preferably 1 to 7 µm. A tablet having a high magnesium oxide particle content of 88 to 97 wt %, preferably 89 to 96 wt %, particularly preferably 90 to 95 wt % is obtained by combining magnesium oxide particles having this particle diameter with a specific binder and disintegrator to be described hereinafter.

The magnesium oxide particles to be tableted may be powdery or granular. When the magnesium oxide particles are granular, they are superior in the effect of preventing the abrasion of a tablet machine and a tablet having a high content of magnesium oxide particles can be obtained.

The magnesium oxide particles are generally obtained by baking magnesium hydroxide particles. It has been found through studies conducted by the inventors of the present invention that magnesium oxide particles obtained by baking magnesium hydroxide having an average secondary particle diameter measured by the laser diffraction scattering method of 1 to 10 µm at 700 to 1,000° C. are not so hard as conventional magnesium oxide particles and do not wear down a tablet machine when a tablet is to be prepared from the magnesium oxide particles.

The binder used in the tablet of the present invention is crystalline cellulose or starch (such as corn starch), and the disintegrator is crosscarmerose sodium, carmerose calcium or carboxy starch sodium. These disintegrators may be used in combination of two or more. Particularly, crosscarmerose sodium and carboxy starch sodium disintegrate in a much smaller amount than conventional disintegrators, thereby making it possible to reduce the amount thereof, rarely change along the passage of time and can provide a tablet having excellent stability. The most preferred disintegrator is crosscarmerose sodium.

The above binder is contained in the tablet in an amount of 1 to 10 wt %, preferably 1 to 8 wt % and the disintegrator is contained in an amount of 1 to 3.5 wt %, preferably 1 to 3 wt %.

According to the present invention, since the amount of the disintegrator can be reduced, the content of the magnesium oxide particles can be thereby increased. Since the above disintegrator rarely changes along the passage of time as described above, a tablet which has excellent stability without reducing the disintegration properties of the disintegrator for a long time after tableting is provided. That is, as will be described hereinafter, even when the tablet is kept at a temperature of 40° C. and a relative humidity (RH) of 75% for 6 months after preparation, it retains a disintegration time of 10 sec or less.

Since powders of magnesium oxide particles which can be molded only by compression at a high pressure at the time of dry granulation are mixed with the above additives (binder and disintegrator) in the present invention, the obtained mixture can be molded into a tablet at a low pressure. As granules molded at a high pressure are hard, when a tablet is made from the granules, it becomes blackish, a tableting spot is formed, and capping and the abrasion of mechanical parts are marked. According to the present invention, there can be provided the following process for producing a tablet, which can prevent these.

A tablet made from granules molded at a high pressure may fail to disintegrate. A tablet which has a short disintegration time and disintegrates quickly in the mouth when it is administered together with water and does not create the sensation of taking a tablet can be obtained by the process of the present invention.

That is, according to the present invention, there is provided a process for producing a tablet comprising magnesium oxide particles as an effective component, comprising the steps of:

a. preparing a mixture consisting of (1) 88 to 97 wt % of magnesium oxide particles having an average secondary particle diameter measured by a laser diffraction scattering method of 0.5 to 10 µm, (2) 1 to 10 wt % of a binder selected from crystalline cellulose and starch and (3) 1 to 3.5 wt % of at least one disintegrator selected from the group consisting of crosscarmerose sodium, carmerose calcium and carboxy starch sodium, b. granulating the mixture to obtain granulated particles having an average particle diameter of 0.25 to 0.4 mm and an apparent density of 0.5 to 0.7 g/ml, and c. mixing 0.2 to 2 wt % of a lubricant with the granulated particles and tableting the mixture.

A description is subsequently given of the tablet production process of the present invention.

First, in the process of the present invention, a raw material mixture is prepared to make a tablet. The raw material mixture consists of (1) 88 to 97 wt % (preferably 89 to 96 wt %) of magnesium oxide particles having an average secondary particle diameter of 0.5 to 10 µm, preferably 1 to 7 µm, (2) 1 to 10 wt % (preferably 2 to 8 wt %) of a binder comprising crystalline cellulose or starch and (3) 1 to 3.5 wt % (preferably 1 to 3 wt %) of at least one disintegrator selected from the group consisting of crosscarmerose sodium, carmerose calcium and carboxy starch sodium.

This raw material mixture is mixed by a container type, V type or W type mixer to be granulated into granulated particles. This granulation can be carried out by using a dry granulator at a low pressure. The granulation is preferably carried out by a roll molding dry granulator and the pressure of the roll is preferably 3 to 12 MPa, more preferably 4 to 8 MPa.

The obtained sheet-like molded product is crushed by an oscillator type crusher to obtain granulated particles. The screen to be mounted on the oscillator has an opening of preferably 0.7 to 1.2 mm, more preferably 0.8 to 1.0 mm.

The granulated particles having an average particle diameter of 0.25 to 0.4 mm and an apparent density of 0.5 to 0.7 g/ml are thus obtained. The particles have a repose angle of 35 to 43°. The granulated magnesium oxide particles having the above average particle diameter and apparent density are tableted to obtain a tablet as an antacid and laxative agent which is the object of the present invention.

The above granulated particles are mixed with a lubricant and supplied into a tablet machine. The used lubricant is, for example, stearic acid or a salt thereof (Na, Mg, Ca salt). It is preferably a stearic acid salt, particularly preferably calcium stearate or magnesium stearate. Calcium stearate is the most effective. When the amount of the lubricant is too large, disintegration is delayed and when the amount is too small, it sticks to a die and punch. Therefore, the amount of the lubricant is preferably 0.2 to 2 wt %, more preferably 0.8 to 1.2 wt %.

According to the process of the present invention, it is desired that the content of fine powders having a particle diameter of 0.10 mm or less be 20 wt % or less, preferably 10 wt % or less when a tablet is made from the granulated particles. It is possible to make a tablet by a tableting operation without removing fine powders. The tableting pressure is preferably 5 to 12 kN, more preferably 6 to 10 kN as a punching pressure per tablet. As for the shape of the punch, it may have a round surface, round corners, flat corners, or round corners/flat surface.

A tablet made by the process of the present invention has no tablet trouble and no tableting spot, does not become blackish, can contain magnesium oxide particles in a large proportion and can be easily taken because it disintegrates quickly in the mouth when it is administered together with water.

The tablet of the present invention has excellent stability and retains a disintegration time of 10 sec or less even after 6 months according to the result of an acceleration test to be described hereinafter.

The size and shape of the tablet of the present invention are the same as those of an ordinary oral tablet. It has a diameter of 5 to 12 mm, preferably 6 to 10 mm, particularly preferably 6 to 9 mm. It has a thickness of preferably 2 to 6 mm, preferably 2 to 5 mm, particularly preferably 2.5 to 4.5 mm. The weight of each tablet is 100 to 1,000 mg, preferably 150 to 800 mg, the most preferably 200 to 600 mg.

The tablet of the present invention is orally administered as an antacid and laxative agent. The dose of the tablet differs according to purpose or the condition of a patient. The standard dose for each adult is 2 g a day. This dose is equivalent to 6 to 8 tablets on the average and can be divided into 1 to 3 portions a day.

The term "blackish" means the blackish tint of the tablet caused by the abrasion between magnesium oxide particles and a mechanical part depending on abrasion of magnesium oxide particles. This refers to a blackish tablet, or the black spot, streak or surface of the tablet.

The term "tablet trouble" means sticking of powders caused by the adhesion of magnesium oxide particles to the punch, or capping caused by the deterioration of a die and punch due to the abrasion of magnesium oxide particles or by the low bonding force of magnesium oxide particles.

The term "tableting spot" means that particles remain on the surface of the tablet as a spot because the particles are hard and difficult to be compressed.

EXAMPLES

The following Examples and Comparative Examples are given to further illustrate the present invention. "%" means "wt %".

The hardness of the tablet, disintegration test, friability, the particle distribution of granules, the average particle diameter of the granules, repose angle, apparent density, abrasion, the stability of the tablet, the disintegration of the tablet in the mouth, dissolution test and laxative function test using animals were conducted and measured in accordance with the following methods.

(a) Hardness of Tablet

The hardness of the tablet was measured using the 6D tablet hardness meter of Schleuniger Co., Ltd. The average value and standard deviation of 10 tablets were obtained.

(b) Disintegration Test

Water was used as a test solution in accordance with the general disintegration test of the 14$^{th}$ edition of the Japanese Pharmacopoeia.

(c) Friability

This is based on the second supplementary and reference information of the 13-th revised Japanese Pharmacopoeia.

(d) Average Secondary Particle Diameter (Magnesium Oxide Particles and Magnesium Hydroxide Particles)

0.7 g of a sample was placed in a 100 ml dry beaker, 70 ml of a 0.2% aqueous solution of sodium hexametaphosphate as a dispersion medium was added, and the resulting solution was pre-treated by an ultrasonic homogeneizer (US-300 of Nippon Seiki Co., Ltd.) to measure its particle distribution by a laser diffraction scattering particle size distribution measuring instrument (Microtrack of Nikkiso Co., Ltd.). The particle diameter value when the total amount of smaller fine particles accounted for 50 wt % of the total was taken as the average secondary particle diameter.

(e) Particle Size Distribution of Granules device: Octagon of Endecotts Co., Ltd.

used screens: 710, 500, 355, 180, 150 and 106 μm test conditions: vibration strength: 5, sifting time: 5 minutes, contact time: 10 sec, suspension time: 2 sec 30 ml of a sample was placed in the top screen of a vessel consisting of a plurality of screens and a receptacle, and the vessel was covered and set in the device. After a test was made under the above conditions, the residues in the screens and the receptacle were measured (up to the unit of 0.01 g).

(f) Average Particle Diameter of Granules

The particle diameter value when the total amount of larger particles accounted for 50 wt % of the total in the above particle size distribution was taken as the average particle diameter.

(g) Repose Angle device: AOR-57 electromagnetic vibration repose angle measuring instrument of Tsutsui Rikagaki Kikai Co., Ltd.

used apparatuses: measurement disk: 8 cm in diameter, net of sample tank: 2 mm

The measurement disk was laid horizontal (height was about 7 cm). The device was turned on. The sample was adjusted so that it fell on the center of the disk and the vibration control dial was adjusted to drop the sample quickly to heap it up mountain-high. A large amount of the sample was dropped at the beginning. When the sample began to overflow from the disk, the guideline of a scale was aligned with a portion which was ⅔ of the inclined side of the mountain from the top. The division of the scale was read as a measurement value.

(h) Apparent Density

The sample was gently put into a 30 ml receptacle used in the JIS K5101 apparent specific volume stationary method with a funnel until it was heaped up mountain-high. The mountain was scraped off with a linear spatula. The mass of the contents of the receptacle was measured up to the unit of 0.01 g.

Apparent density (g/ml)=F/30

F: mass of sample in receptacle (g)

30: capacity of receptacle (ml)

(i) Abrasion

The blackish tint and tableting spot of the tablet were observed with the eyes.

(j) Stability of Tablet

The tablet was covered with a sheet consisting of four polyvinyl chloride layers (polyvinyl chloride, polyvinylidene chloride, polypropylene and polyvinyl chloride layers), pillow-packaged in an aluminum foil and subjected to an acceleration test for 6 months (40° C., 75 RH %) to investigate the influence upon stability of disintegration. The results are shown in Table 2.

(k) Disintegration in Mouth

A disintegration test was made on the tablet in the mouths of 12 healthy people. The people held one sip of water in their mouths and took one tablet. The period of time before they lost the sensation of taking a tablet was measured. The results are shown in Table 3.

(l) Dissolution Test

An dissolution test was made on the magnesium oxide tablets of Examples 1 and 3 in accordance with the second puddle method of a dissolution test specified by the 14$^{th}$ edition of the Japanese Pharmacopoeia (test solution: first solution of the disintegration test method of the Japanese Pharmacopoeia, solution temperature: 37° C., revolution: 50 rpm, measurement time: 60 minuets). The results are shown in Table 4.

(m) Laxative Effect Test Using Animals

A laxative effect test was made using mice.

(Preparation of Test Sample)

The tablets of Examples 1 and 3 were crushed and suspended in 0.5% CMC to prepare test samples.

(Animal)

4 week old ICR-based male mice (SPF) were checked for their health conditions visually when they arrived and acclimated for 1 week during which their general conditions were observed and 5 week old mice which were well grown out of these were used.

(Grouping Table)

Table 5 shows the groups of mice used in the animal test.

(Test Method)

The mice were given no food for 12:00 to 17:00 the day before the test and then fed solid food. On the test day, each mouth was put in a metal net cage having a bat covered with water absorbing paper and observed for 30 minutes before administration. After the test sample was orally administered to the mice using a disposable injection cylinder and an oral zonde forcedly, the mice were observed every 1 hour for 12 hours after administration and the conditions of the excretions of the mice (the time when a loose passage or diarrhea occurred and the number of mice which suffered from a loose passage or diarrhea) were checked for 24 hours finally. Feed and water were continuously given to the mice during the test period.

The results are shown in Table 6.

Example 1

Prescription Example 1

| | |
|---|---|
| Magnesium oxide particles | 330 mg (88%) |
| Crystalline cellulose | 23 mg (6.1%) |
| Corn starch | 7 mg (1.9%) |
| Crosscarmerose sodium | 11 mg (2.9%) |
| Calcium stearate | 4 mg (1.1%) |
| One tablet | 375 mg |

(Production Method)

39.6 kg of magnesium oxide particles having an average secondary particle diameter of 6.5 μm, 2.76 kg of crystalline cellulose, 0.84 kg of corn starch and 1.32 kg of crosscarmerose sodium were mixed together by a container type mixer, the resulting mixture was granulated by a roll molding dry granulator at a roll pressure of 5 MPa, and the obtained molded product was crushed by an oscillator type crusher to prepare granules. 40.81 kg of the granules and 0.44 kg of calcium stearate were mixed together by a container type mixer to produce granules which were then tableted by a rotary tablet machine having 36 13R punches with a diameter of 9 mm at a tableting pressure of 9 kN to make a magnesium oxide tablet having a weight of 375 mg and a thickness of 4.8 mm. The hardness, disintegration time and abrasion of the tablet are shown in Table 1.

As for the grain size distribution of the granules, granules having a size of 0.71 to 0.81 mm accounted for 1.4% of the total, those having a size of 0.50 to 0.71 mm accounted for 27.3%, those having a size of 0.355 to 0.50 mm accounted for 20.6%, those having a size of 0.18 to 0.355 mm accounted for 32.3%, those having a size of 0.15 to 0.18 mm accounted for 7.8%, those having a size of 0.106 to 0.15 mm accounted for 7.1%, and those having a size of 0.106 mm or less accounted for 3.4% when a 0.81 mm screen was used, and the granules had an average particle diameter of 0.349 mm, a repose angle of 38° and an apparent density of 0.60 g/ml.

Example 2

Prescription Example 2

| | |
|---|---|
| magnesium oxide particles | 330 mg (91.7%) |
| crystalline cellulose | 11 mg (3.1%) |
| corn starch | 7 mg (1.9%) |
| crosscarmerose sodium | 8 mg (2.2%) |
| calcium stearate | 4 mg (1.1%) |
| one tablet | 360 mg |

(Production Method)

39.6 kg of magnesium oxide particles having an average secondary particle diameter of 6.5 μm, 1.32 kg of crystalline cellulose, 0.84 kg of corn starch and 0.96 kg of crosscarmerose sodium were mixed together by a container type mixer, the resulting mixture was granulated by a roll molding dry granulator at a roll pressure of 6 MPa, and the obtained molded product was crushed by an oscillator type crusher to prepare granules. 39.16 kg of the granules and 0.44 kg of calcium stearate were mixed together by a container type mixer to produce granules which were then tableted by a rotary tablet machine having 36 13R punches with a diameter of 9 mm at a tableting pressure of 8.5 kN to obtain a magnesium oxide tablet having a weight of 360 mg and a thickness of 4.4 mm. The hardness, disintegration time and abrasion of the tablet are shown in Table 1.

As for the grain size distribution of the granules, granules having a size of 0.71 to 0.81 mm accounted for 0.1% of the total, those having a size of 0.50 to 0.71 mm accounted for 12.6%, those having a size of 0.355 to 0.50 mm accounted for 22.3%, those having a size of 0.18 to 0.355 mm accounted for 33.6%, those having a size of 0.15 to 0.18 mm accounted for 7.6%, those having a size of 0.106 to 0.15 mm accounted for 11.8%, and those having a size of 0.106 mm or less accounted for 12.0% when a 0.81 mm screen was used, and the granules had an average particle diameter of 0.262 mm, a repose angle of 40° and an apparent density of 0.65 g/ml.

Example 3

Prescription Example 3

| | |
|---|---|
| magnesium oxide particles | 255 mg (89.5%) |
| crystalline cellulose | 15 mg (5.3%) |
| corn starch | 5 mg (1.8%) |
| crosscarmerose sodium | 7 mg (2.5%) |
| calcium stearate | 3 mg (1.1%) |
| one tablet | 285 mg |

(Production Method)

38.25 kg of magnesium oxide particles having an average secondary particle diameter of 6.5 μm, 2.25 kg of crystalline cellulose, 0.75 kg of corn starch and 1.05 kg of crosscarmerose sodium were mixed together by a container type mixer, and the resulting mixture was tableted by a rotary tablet machine having 36 12R punches with a diameter of 8 mm at a tableting pressure of 7.5 kN to obtain a magnesium oxide tablet having a weight of 285 mg and a thickness of 4.5 mm. The hardness, disintegration time and abrasion of the tablet are shown in Table 1.

Example 4

A magnesium oxide tablet was obtained based on the same prescription using the same steps and devices as in Example 1 except that magnesium oxide particles having an average secondary particle diameter of 3.6 μm were used. The hardness, disintegration time and abrasion of the tablet are shown in Table 1.

As for the grain size distribution of the granules, granules having a size of 0.71 to 0.81 mm accounted for 0.8% of the total, those having a size of 0.50 to 0.71 mm accounted for 33.9%, those having a size of 0.355 to 0.50 mm accounted for 18.7%, those having a size of 0.18 to 0.355 mm accounted for 18.2%, those having a size of 0.15 to 0.18 mm accounted for 3.0%, those having a size of 0.106 to 0.15 mm accounted for 5.5%, and those having a size of 0.106 mm or less accounted for 19.8% when 0.81 mm screen was used, and the granules had an average particle diameter of 0.378 mm, a repose angle of 41° and an apparent density of 0.67 g/ml.

Comparative Example 1 (Direct Tableting Method Using Granulated Magnesium Oxide Particles)

Prescription Example 4

| magnesium oxide particles | 330 mg (89.9%) |
|---|---|
| crystalline cellulose | 18 mg (4.9%) |
| crosscarmerose sodium | 15 mg (4.1%) |
| calcium stearate | 4 mg (1.1%) |
| one tablet | 367 mg |

(Production Method)

33.0 kg of magnesium oxide particles having an average secondary particle diameter of 6.50 μm, 1.8 kg of crystalline cellulose and 1.5 kg of crosscarmerose sodium were mixed together by a container type mixer, and 0.4 kg of calcium stearate was further added and mixed by the above mixer to produce granules. The granules were tableted by a rotary tablet machine having 36 13R punches with a diameter of 9 mm at a tableting pressure of 9 kN to make a magnesium oxide tablet having a weight of 367 mg and a thickness of 4.1 mm.

TABLE 1

|  | Ex. 1 | Ex. 2 | Ex. 3 | Ex. 4 | C. Ex. 1 |
|---|---|---|---|---|---|
| Weight of each tablet (mg) | 375 | 360 | 285 | 375 | 367 |
| Hardness of tablet (N) | >70 | >110 | >70 | >60 | >40 |
| Disintegration time (sec) | 7 | <7 | 6 | 8 | 20 |
| Friability (%) | <0.3 | <0.3 | <0.1 | <0.5 | 0.8 |
| abrasion  Blackish tint | not seen | not seen | not seen | not seen | seen |
|          Tableting spot | not seen | not seen | not seen | not seen | seen |

Ex.: Example
C. Ex.: Comparative Example

TABLE 2 stability of pharmaceutics

|  |  | Ex. 1 | Ex. 3 | C. Ex. 1 |
|---|---|---|---|---|
| Disintegration time (sec) | Before acceleration test | 7 | 6 | 20 |
|  | After 2 months | 7 | 7 | 455 |
|  | After 4 months | 9 | 8 | 1024 |
|  | After 6 months | 8 | 8 | >1800 |

Ex.: Example
C. Ex.: Comparative Example

TABLE 3 disintegration in mouth

|  | Number of people | |
|---|---|---|
|  | Ex. 1 | Ex. 3 |
| 6 sec | 0 | 3 |
| 7 sec | 1 | 4 |
| 8 sec | 6 | 5 |
| 9 sec | 5 | 0 |

Ex.: Example

The disintegration of the tablet of Comparative Example 1 which was produced from magnesium oxide particles by a direct tableting method was affected by an acceleration test along the passage of time and the disintegration time of the tablet was markedly prolonged.

In Examples 1 and 3, the results of the disintegration tests in the mouth were almost the same as the results of the disintegration test. When the tablet was administered together with water, the sensation of taking a tablet was lost within 10 seconds. Therefore, the tablet was easily taken. The tablet of the present invention can be taken even by a patient which has difficulties of swallowing a medicine.

TABLE 4 dissolution test

|  | dissolution rate | |
|---|---|---|
| Time (minutes) | Ex. 1 | Ex. 3 |
| 5 | 34.8 | 33.0 |
| 10 | 57.1 | 80.1 |
| 15 | 85.5 | 92.0 |
| 30 | 101.1 | 103.9 |
| 45 | 111.0 | 104.0 |
| 60 | 108.6 | 103.5 |

Ex.: Example

The tablets of Examples 1 and 3 showed an dissolution rate of 85% or more in 15 minutes.

TABLE 5

| Group | dose (mg/mL) | dose of solution (mL/kg) | number of mice |
|---|---|---|---|
| Control (0.5% CMC) | — | 10 | 10 |
| Ex. 1 | 250 | 10 | 10 |
| Ex. 2 | 250 | 10 | 10 |

Ex.: Example

TABLE 6 laxative effect test using animals

Number of mice which suffer from a loose passage or diarrhea
Time

| Group | 1 | 2 | 3 | 4 | 5 | 6 | 7 | 8 | 9 | 10 | 11 | 12 | 24 |
|---|---|---|---|---|---|---|---|---|---|---|---|---|---|
| Control group | 0 | 0 | 0 | 0 | 0 | 0 | 0 | 0 | 0 | 0 | 0 | 0 | 0 |
| Ex. 1 | 4 | 6 | 9 | 9 | 10 | 8 | 5 | 3 | 1 | 0 | 0 | 0 | 0 |
| Ex. 3 | 4 | 6 | 9 | 10 | 10 | 8 | 4 | 2 | 1 | 0 | 0 | 0 | 0 |

Ex.: Example

A loose passage was observed in all the mice 9 hours after the administration of the test sample in Examples 1 and 3 and the peak time when the loose passage occurred was 3 to 5 hours. Meanwhile, a loose passage was not observed in all the mice of the control group during the test. The tablets of Examples 1 and 3 of the present invention showed a laxative effect.

The invention claimed is:

1. An antacid and laxative tablet comprising magnesium oxide particles as an effective component, wherein
   (i) the magnesium oxide particles contained in the tablet have an average secondary particle diameter measured by a laser diffraction scattering method of 0.5 to 10 μm,
   (ii) the content of magnesium oxide particles in the tablet is 88 to 97 wt %,
   (iii) the tablet does not become blackish and has substantially no tableting spot,
   (iv) the disintegration time is 10 second or less,
   (v) the magnesium oxide particles are obtained by baking magnesium hydroxide particles having an average secondary particle diameter of 1 to 10 μm measured by a laser diffraction scattering method at 700 to 1000° C.,
   (vi) the tablet contains 1 to 10 wt % of crystalline cellulose or starch as a binder,
   (vii) the tablet contains 1 to 3.5 wt % of at least one selected from the group consisting of crosscarmerose sodium, carmerose calcium, and carboxy starch sodium as a disintegrator,
   (viii) the tablet is formed from granulated magnesium oxide particles having an average particle diameter of 0.25 to 0.40 mm, and
   (ix) the tablet is formed from granulated magnesium oxide particles having a repose angle of 35 to 43°.

2. The antacid and laxative tablet of claim 1, wherein the magnesium oxide particles have an average secondary particle diameter measured by the laser diffraction scattering method of 1 to 7 μm.

3. The antacid and laxative tablet of claim 1, wherein the content of the magnesium oxide particles in the table is 89 to 96 wt %.

4. The antacid and laxative tablet of claim 1 which contains 1 to 3.5 wt % of crosscarmerose sodium or carboxy starch sodium as a disintegrator.

5. The antacid and laxative tablet of claim 1, wherein the magnesium oxide particles are formed from granulated magnesium oxide particles which are dry granulated together with a binder and/or a disintegrator as required at a pressure of 4 to 8 MPa.

6. The antacid and laxative tablet of claim 1 which is formed from granulated magnesium oxide particles having an apparent density of 0.50 to 0.70 g/ml.

7. The antacid and laxative tablet of claim 1 which has a disintegration time of 10 second or less when it is kept at a temperature of 40° C. and a relative humidity of 75% for 6 months after it is tableted.

8. A process for producing a tablet comprising magnesium oxide particles as an effective component, comprising the steps of:
   a. preparing a mixture comprising of (1) 88 to 97 wt % of magnesium oxide particles having an average secondary particle diameter measured by a laser diffraction scattering method of 0.5 to 10 μm, (2) 1 to 10 wt % of a binder selected from crystalline cellulose and starch, and (3) 1 to 3.5 wt % of at least one disintegrator selected from the group consisting of crosscarmerose sodium, carmerose calcium and carboxy starch sodium;
   b. granulating the mixture to obtain granulated particles having an average particle diameter of 0.25 to 0.4 mm and an apparent density of 0.5 to 0.7 g/ml; and
   c. mixing the granulated particles with 0.2 to 2 wt % of a lubricant and tableting the resulting mixture wherein the tablet has a disintegration time of 10 seconds or less.

9. The process for producing a tablet of claim 8, wherein the granulated particles are tableted at a punching pressure of 5 to 12 kN per tablet.

* * * * *